United States Patent
Drazek et al.

(10) Patent No.: US 10,655,159 B2
(45) Date of Patent: May 19, 2020

(54) MEANS, METHOD AND COMPUTER PROGRAM PRODUCT FOR DETERMINING THE CONCENTRATION LEVEL OF MICROORGANISMS DURING A FLUID ANALYSIS

(71) Applicant: BIOMERIEUX, Marcy-l'Etoile (FR)

(72) Inventors: Laurent Drazek, Grenoble (FR); Corine Fulchiron, Serrieres de Briord (FR); Frederic Pinston, Grenoble (FR); Herve Rostaing, Le Versoud (FR)

(73) Assignee: BIOMERIEUX, Marcy-l'Etoile (FR)

( * ) Notice: Subject to any disclaimer, the term of this patent is extended or adjusted under 35 U.S.C. 154(b) by 0 days.

(21) Appl. No.: 16/298,708

(22) Filed: Mar. 11, 2019

(65) Prior Publication Data
US 2019/0203258 A1    Jul. 4, 2019

Related U.S. Application Data

(62) Division of application No. 14/762,103, filed as application No. PCT/EP2014/050999 on Jan. 20, 2014, now Pat. No. 10,465,225.

(30) Foreign Application Priority Data

Jan. 21, 2013    (FR) .................................... 13 50503

(51) Int. Cl.
*C12Q 1/06* (2006.01)
*C12M 1/22* (2006.01)
(Continued)

(52) U.S. Cl.
CPC ............... *C12Q 1/06* (2013.01); *C12M 23/10* (2013.01); *C12M 33/02* (2013.01); *C12Q 1/24* (2013.01); *G01N 2333/195* (2013.01)

(58) Field of Classification Search
CPC ............ C12Q 1/06; C12Q 1/24; C12M 23/10; C12M 33/02; G01N 2333/195
See application file for complete search history.

(56) References Cited

U.S. PATENT DOCUMENTS

| | | |
|---|---|---|
| 2,971,892 A | 2/1961 | Carski |
| 3,892,632 A | 7/1975 | Campbell et al. |

(Continued)

FOREIGN PATENT DOCUMENTS

| | | |
|---|---|---|
| WO | 2005071055 A1 | 8/2005 |
| WO | 2008093439 A1 | 8/2008 |
| WO | 2014111559 A1 | 7/2014 |

OTHER PUBLICATIONS

Gilchrist et al., Sprial Plate Method for Bacterial Determination, Applied Microbiology, Feb. 1973, p. 244-252, vol. 25, No. 2.

(Continued)

*Primary Examiner* — William H. Beisner
*Assistant Examiner* — Danielle B Henkel
(74) *Attorney, Agent, or Firm* — Pepper Hamilton LLP (57) ABSTRACT

A locating method and system of determining a microorganism concentration of a fluid in a Petri dish is disclosed. The Petri dish includes a culture medium on which a seeding device is rotatable relative to the Petri dish. The seeding device distributes the fluid and includes at least one point of contact with the culture medium. The point of contact is associated with a contact zone.

5 Claims, 12 Drawing Sheets

(51) Int. Cl.
*C12M 1/30* (2006.01)
*C12Q 1/24* (2006.01)

(56) References Cited

U.S. PATENT DOCUMENTS

| | | | |
|---|---|---|---|
| 4,273,877 A | | 6/1981 | Anagnostopoulos |
| 4,353,988 A | | 10/1982 | Couse et al. |
| 4,514,495 A | | 4/1985 | Schalkowsky et al. |
| 4,517,292 A | | 5/1985 | Schalkowsky et al. |
| 4,637,053 A | | 1/1987 | Schalkowsky |
| 5,694,478 A | * | 12/1997 | Braier ............... C12Q 1/04 |
| | | | 382/133 |
| 5,928,858 A | | 7/1999 | Chao |
| D582,564 S | | 12/2008 | Potter et al. |
| 8,787,633 B2 | | 7/2014 | Robinson et al. |
| 2007/0202564 A1 | * | 8/2007 | Glasson ............ C12M 33/02 |
| | | | 435/30 |
| 2012/0076409 A1 | | 3/2012 | Guo |
| 2015/0353983 A1 | * | 12/2015 | Drazek ............... C12Q 1/06 |
| | | | 435/39 |

OTHER PUBLICATIONS

International Search Report and Written Opinion for PCT/EP2014/050999, dated Feb. 24, 2014.

* cited by examiner

C=10$^5$ CFU/ml

C=10$^6$ CFU/ml

*FIG. 10*

$C=10^7$ CFU/ml $C=10^8$ CFU/ml

MEANS, METHOD AND COMPUTER PROGRAM PRODUCT FOR DETERMINING THE CONCENTRATION LEVEL OF MICROORGANISMS DURING A FLUID ANALYSIS

CROSS-REFERENCE TO RELATED APPLICATIONS

This application is a Divisional filing of U.S. patent application Ser. No. 14/762,103 filed on Jul. 20, 2015, which is a U.S. national stage filing under 35 U.S.C. § 371 of International application No. PCT/EP2014/050999 filed on Jan. 20, 2014 that claims the benefit of French Application No. 1350503 filed on Jan. 21, 2013. Each of the aforementioned applications are incorporated herein by reference in its entirety.

TECHNICAL FIELD

The present invention relates to the field of biological analysis and, more precisely, a means, a method and a computer software package for determining the concentration level of microorganisms present in a fluid, during the analysis of a sample of this fluid.

STATE OF THE ART

In the field of biological analysis, there exist numerous methods for determining the concentration levels of microorganisms in biological samples. These methods are notably applied by using a Petri dish and a seeding device, such as a suitable comb as described in patent applications WO2005/071055 and WO2008/093439.

Thus, in the prior art, the Petri dish contains a culture medium such as an agar medium. A fluid sample comprising microorganisms is introduced onto the culture medium. The fluid is applied in a strip which extends from the centre of the Petri dish to the edge of the Petri dish. The length of this strip of fluid therefore extends in the direction of the radius of the Petri dish. Then, in the case of a manual or automatic seeding, a comb, such as described in patent applications WO2005/071055 and WO2008/093439, moves the microorganisms amassed within the strip of fluid, onto the entire circumference of the Petri dish. The comb, which is situated above the Petri dish, can move in an axis perpendicular to the plane of the Petri dish, said Petri dish being able to rotate on its own axis. Generally, the width of the comb corresponds approximately to the radius of the Petri dish. The comb is positioned such that a first tooth of the comb is situated at the centre of the Petri dish and a last tooth of the comb is situated close to the edge of the Petri dish. Thus the comb makes it possible to distribute the contents of the strip of fluid at an angle from 0° to approximately 330° within the culture medium.

In the case of a manual or automatic seeding, several methods of determining the microorganism concentration are applicable. One of these methods employs a division of the Petri dish into eight sectors, i.e. into octants, on a ChromID™ CPS® medium (Ref. 43541) for the identification and the counting of urinary germs. Thus, when the user wishes to evaluate the bacterial concentration level of the fluid distributed on the culture medium, the user estimates the culture medium cover rate in each octant, then uses a chart which has been previously drawn up and supplied to the user. This method is laborious because the user must survey all the colonies present in all of the octants. This surveying can therefore generate counting errors, and consequently errors in terms of the bacterial concentration level to be determined.

As the comb moves, the distribution of the fluid on the culture medium is not homogenous within a given sector, depending on the comb tooth under consideration. Indeed, for an angle of rotation associated with the movement of the comb, the comb teeth travel a distance which varies depending on the location of the teeth on the comb. If we consider the teeth situated close to the centre of the Petri dish, the azimuthal distance travelled by these teeth is less than the azimuthal distance travelled by teeth situated close to the edge of the Petri dish, for an identical angle of rotation of the comb on the culture medium.

Thus, applying the method which employs the division of the Petri dish into eight sectors, the distance travelled by the fluid for a sector under consideration depends on the comb tooth associated with the movement of said fluid. Consequently, each sector contains a quantity of fluid of which the bacteria concentration is variable on the surface of a given sector.

The non-homogenous distribution of the fluid within different sectors also generates measurement errors when determining the microorganism concentration present in the fluid to be analysed. Thus, this method does not make it possible to precisely determine the microorganism concentration within the fluid.

STATEMENT OF THE INVENTION

The present invention is aimed at overcoming the above-mentioned problems at least in part.

An objective of the present invention consists in supplying a locating means for determining the microorganism concentration of a fluid to be analysed by means of a Petri dish, said Petri dish comprising a culture medium on which a seeding device able to rotate relative to the Petri dish is fitted so as to distribute the fluid, said seeding device comprising at least one point of contact associated with a contact zone with said culture medium, said locating means comprising:

- a circle C1 corresponding to the circumference of the Petri dish, the circle C1 comprising a centre O and a radius RC1 corresponding to the radius of the Petri dish;
- a seeding line LR of length R representing the zone for inoculating the fluid on the culture medium and corresponding to a portion of the radius RC1 of the Petri dish;
- at least one locating zone Zn for locating the presence of microorganisms on the culture medium,
    said locating zone Zn being delimited by the seeding line LR and a zone boundary line LZ delimiting an identical distance d travelled on the surface of the culture medium by each point of contact of the contact zone of the seeding device starting from the seeding line LR.

Advantageously, the fluid comprises a microorganism concentration greater than $10^3$ microorganisms per millilitre (ml).

Advantageously, each locating zone Zn corresponds to a predetermined value of the microorganism concentration of the fluid.

Advantageously, the predetermined value is defined by an exponential function of the angle of rotation of the seeding device, of the length R of the seeding line and of a constant defining the depletion rate of the bacterial concentration in the fluid as a function of the distance travelled on the culture medium.

Advantageously, the locating zone Zn is delimited by the circle C1 and by a circle of radius RC2 which is concentric to circle C1 and such that RC2 is smaller than RC1.

Advantageously, the zone boundary line LZ is formed by a set of points Pn, each point Pn being situated on a circle Cn concentric to circle C1, said circle Cn comprising a radius RCn, such that RCn is smaller than RC1 and greater than RC2, and each point Pn being situated at an equal distance from the seeding line LR for a same zone boundary line LZ.

Advantageously, the microorganisms comprise bacteria.

Advantageously, the culture medium comprises an agar medium.

Advantageously, the fluid consists of a sample of clinical, food, environmental, veterinary, pharmaceutical or cosmetic origin.

Another objective of the invention consists in supplying a locating method for determining the microorganism concentration of a fluid to be analysed by means of a Petri dish with radius RC1, said Petri dish comprising a culture medium, said method comprising the following steps:

depositing the fluid on the culture medium to form a seeding line LR corresponding to a portion of the radius RC1 of the Petri dish;

distributing the fluid contained in the seeding line LR onto the culture medium by means of a seeding device able to rotate relative to the Petri dish, said seeding device comprising at least one point of contact with the culture medium;

incubating the Petri dish to permit the growth of the microorganisms on the culture medium;

identifying adjacent locating zones Zn to locate the presence of microorganisms on the culture medium, said locating zones Zn covering at least part of the surface of the Petri dish, and in which a first locating zone Zn is delimited by the seeding line LR and a zone boundary line LZ delimiting a same distance d travelled on the culture medium, by each point of contact of the seeding device starting from the seeding line LR.

Advantageously, the fluid comprises a microorganism concentration greater than $10^3$ microorganisms per millilitre (ml).

Advantageously, the locating method comprises the following step:

identifying a locating zone Zn comprising isolated colonies of microorganisms.

Advantageously, the locating method comprises the following step:

finding, in a correspondence table, a predetermined value for microorganism concentration associated with the identified locating zone Zn in order to determine the microorganism concentration in the fluid.

Another objective of the invention consists in supplying a computer software package comprising software instructions for implementing an above-mentioned locating method when said program is executed by a data processor.

BRIEF DESCRIPTION OF THE DRAWINGS

The invention, its functionality, its applications and its advantages shall be better understood upon reading the present description, made with reference to the figures, wherein.

DETAILED DESCRIPTION OF THE INVENTION

The detailed description below aims to set out the invention in a manner which is sufficiently clear and complete, notably with the aid of examples, but must by no means be regarded as limiting the scope of protection to the particular embodiments and to the examples presented below.

The present invention relates to the analysis of a sample. According to the present invention, the sample may be from various origins, for example of food, environmental, veterinary, clinical, pharmaceutical or cosmetic origin.

Amongst the samples of food origin, non-exhaustive mention can be made of a sample of dairy products (yogurts, cheeses), meat, fish, egg, fruit, vegetable, water, beverages (milk, fruit juice, soft drink, etc.). Of course, these samples of food origin can also come from sauces or more complex dishes, or from processed or partially processed raw materials. A food sample can also come from an animal feed, such as oil meals or animal meals.

As indicated previously, the sample can be of environmental origin and can consist, for example, of a surface sample, water sample, air sample, etc.

The sample can also consist of a sample of clinical origin, which can correspond to specimens of biological fluid (urine, whole blood or derivatives such as serum, saliva, pus, cerebrospinal fluid, etc.), of stools (for example cholera-induced diarrhoea), of specimens from the nose, throat, skin, wounds, organs, tissues or isolated cells. This list is obviously not exhaustive.

Generally, the term "sample" refers to a part or a quantity, and more particularly a small part or a small quantity, taken from one or more entities for the purpose of analysis. This sample can possibly have undergone pretreatment, involving for example steps of mixing, diluting or even crushing, in particular if the starting entity is in the solid state.

The sample collected is, in general, capable of—or suspected of—containing at least one target external microorganism such as a bacterium, a yeast or a fungus.

According to the present invention, the analysis is carried out using a Petri dish comprising a base and a lid. The base comprises a culture medium such as an agar culture medium. The aim of the analysis is to determine the presence of specific microorganisms and the concentration of microorganisms within the fluid on the culture medium, after incubation of the Petri dish.

The present invention proposes determining the concentration of the microorganisms present on the culture medium by locating the colonies of microorganisms isolated on said culture medium.

Figure 1:
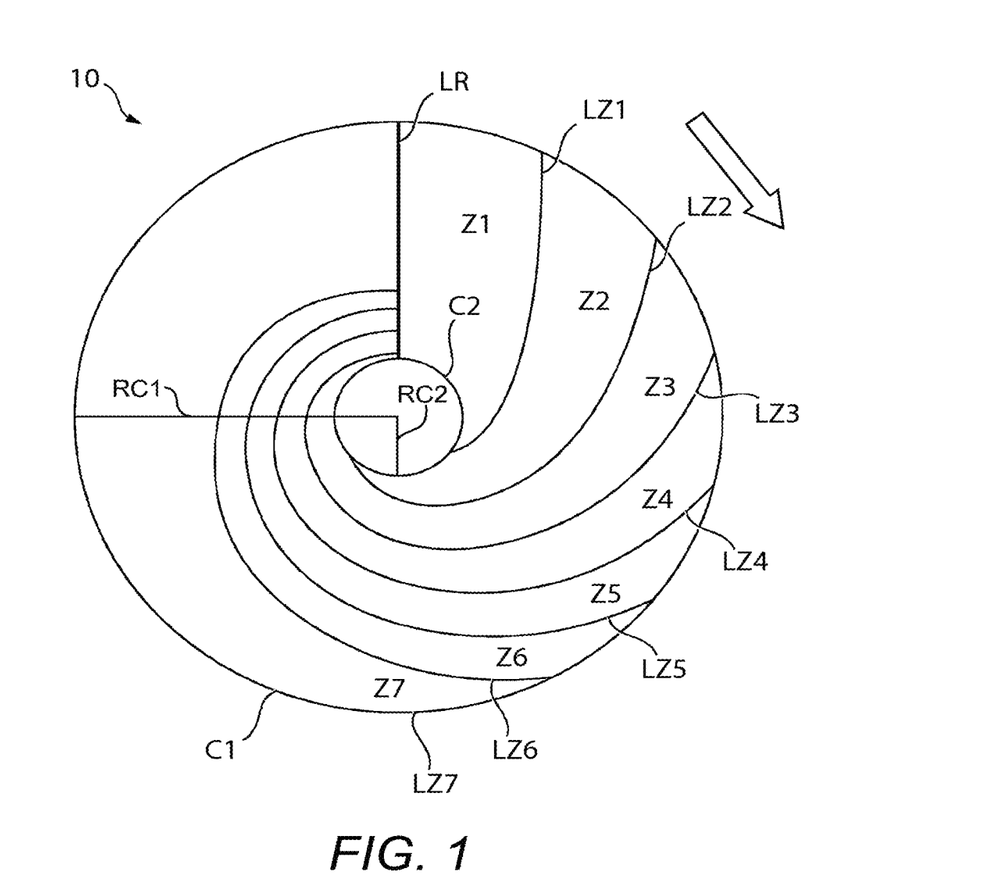
FIG. 1 shows a schematic representation of a locating means, according to an embodiment of the invention, by way of example.

FIG. 1 shows a locating means 10. This locating means 10 can be made from a translucent material in order to be placed on the lid of a Petri dish to observe the agar culture medium containing the microorganisms. The locating means 10 can also be integrated into the lid of a Petri dish by means of a graphic method, for example. Finally, the locating means 10 can also be integrated within a computer software in order to enable analysis of the microorganism presence by means of a computer.

The locating means 10 comprises a circle C1, the dimensions of which are of the same order of magnitude as the dimensions of a circle representing the base of a Petri dish. The circle C1 comprises a centre O and a radius RC1.

The locating means 10 also comprises a circle C2 which is concentric to circle C1 and the radius RC2 such that radius RC2 is smaller than radius RC1.

Circle C1 also comprises a seeding line LR of length R extending in the direction of radius RC1, and such that the length R is smaller than or equal to the value of the difference between radii RC1 and RC2, i.e. R<RC1−RC2. The seeding line LR represents a reference line along which a strip of fluid to be analysed is inoculated on the culture medium.

A seeding device makes it possible to move the fluid from the seeding line LR, onto all or a part of the surface of the agar culture medium on the base of the Petri dish. The length R of the seeding line LR is generally smaller than or equal to the width of the seeding device. The seeding device comprises a contact zone with the agar culture medium. The contact zone comprises at least one point of contact with the agar culture medium via the fluid situated between the point of contact and the culture medium. The contact zone may be, for example, continuous or discontinuous.

The seeding device comprises for example a comb such as described in patent applications WO2005/071055 and WO2008/093439. Each tooth of the comb corresponds to one point of contact. Thus the comb teeth as a group represent a discontinuous contact zone with the culture medium.

The seeding device can also comprise a spatula with curved end such as described in the model U.S. D582,564. Thus, the curved end represents a continuous contact zone of the seeding device with the agar culture medium.

During the distribution of the fluid on the culture medium by means of the seeding device, each point of contact of the contact zone of the seeding device travels an azimuthal distance starting from the seeding line LR. This azimuthal distance varies according to the point of contact under consideration of the contact zone of the seeding device.

The locating means 10 also comprises a set of locating zones Zn which cover all or a part of the surface of the agar culture medium within the surface delimited by the circles of radii RC1 and RC2. These zones are numbered from Z1 to Z7, for example. Each locating zone Zn comprises a zone boundary line LZ, which makes it possible to separate two adjacent locating zones. The disc associated with circle C2 represents a surface which is non-useable for the seeding device. Indeed, for radius values smaller than the value of RC2, in the disc of radius RC2, the azimuthal distances travelled by the points of contact of the contact zone of the seeding device are too small to make it possible to determine the microorganism concentration using the locating means according to the present invention.

The zone boundary lines LZ are labelled LZ1 to LZ7, for example. These lines are made on the locating means 10 using a method illustrated in FIG. 2.

Figure 2:
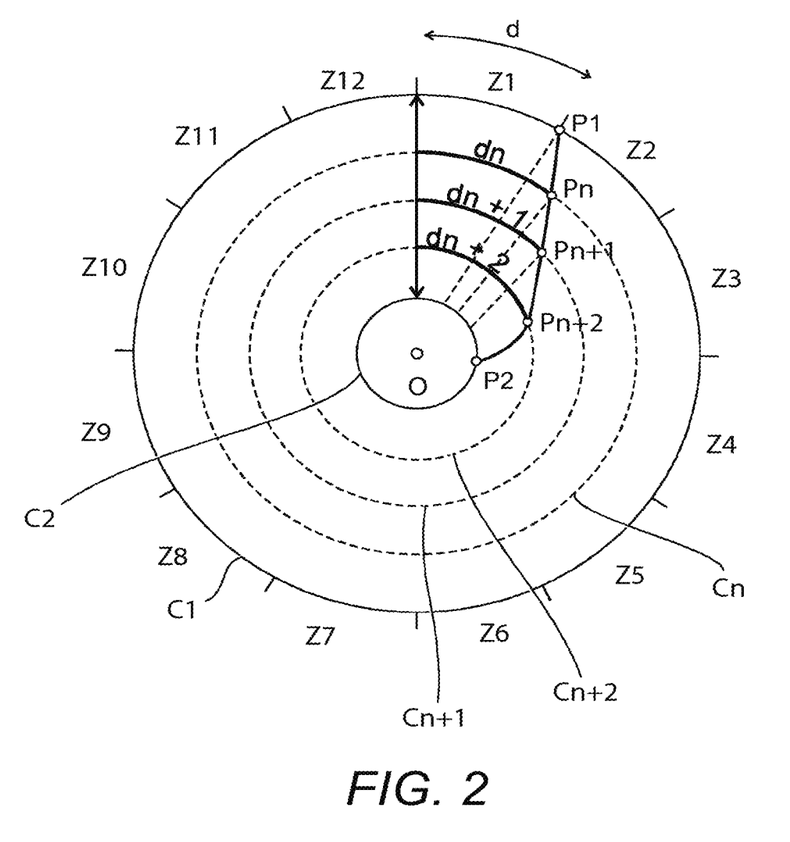
FIG. 2 shows an initial detailed schematic representation of a locating means under development, according to an embodiment of the invention, by way of example.

FIG. 2 shows the locating means 10 during its development to obtain the representation of the zone boundary lines LZ.

The locating means 10 comprises circles C1 and C2 as previously indicated.

In order to develop the locating means 10, concentric circles Cn of radius RCn and centre O are traced onto the locating means 10. The circles Cn are such that each radius RCn is smaller than radius RC1 and greater than radius RC2. The presence of the graphic representation of the circles Cn is not necessary during the subsequent use of the locating means 10.

The circumference of circle C1 is divided into a determined number of circle portions, where each circle portion represents an azimuthal distance d. The azimuthal distance d corresponds to a movement of the points of contact of the contact zone of the seeding device from the seeding line LR, during a rotation of the seeding device. Ai is defined as being the real or effective angle of rotation of the seeding device on circle C1 relative to the seeding line LR. Each azimuthal distance d on circle C1 delimits the locating zones as Z1 to Z7. Thus, each locating zone Zn is delimited, on the circumference of circle C1, by an azimuthal distance which is a multiple of the azimuthal distance d and preferably equal to the azimuthal distance d.

Thus, in a known manner, the portion d represents an azimuthal distance equal to the product of distance R, lower than or equal to the difference RC1−RC2 and representing the length of the seeding line LR, by the angle of rotation Ai which is predetermined and associated with the rotation of the seeding device during the movement of the seeding device on the circumference of circle C1. Thus, we obtain $d = R \times Ai$.

One of the aims of the present invention is to supply a locating means 10 which makes it possible to locate the zones of the culture medium in which isolated colonies of microorganisms are observed. Thus, the locating means 10 makes it possible to determine the initial concentration of microorganisms in the fluid of interest, i.e. the carrier liquid containing the bacteria.

For each circle Cn, an azimuthal distance dn is located. This distance dn is the representation of the azimuthal distance travelled by the points of contact of the contact zone of the seeding device on a specific circle Cn during the rotation of the seeding device by an angle Ai.

The azimuthal distance dn is therefore equal to a multiple of the azimuthal distance d, the value of which is defined by a determined value. Thus, by referring to the known value of d, we obtain $dn = (R \times Ai) \times k$, where k is a number representing the coefficient relative to the multiplicity of d relative to dn.

Aj is defined as being the fictitious angle of rotation of the seeding device on a circle Cn relative to the seeding line LR for a point of contact situated at a distance Rn from the centre O, such that the azimuthal distance dn is equal to d for a specific circle Cn.

The azimuthal distance dn is also equal to the product of radius Rn by the angle of rotation Aj associated with the rotation of a point of contact of the contact zone of the seeding device, i.e. dn=Rn×Aj. The value of dn corresponds to the distance travelled by a point of contact of the contact zone of the seeding device on the concentric circle Cn during the rotation of the seeding device by an angle Aj. Each portion dn makes it possible to represent the distance or path that each point of contact of the contact zone must travel on a given circle Cn to obtain an azimuthal distance travelled and relative to the zone Zn under consideration such that dn is equal to d.

The value of d is therefore determinable insofar as the values of the angle of rotation Ai of the seeding device and of the radius R associated with the length of the seeding line are known. By using Aj=dn/Rn, the value of the angle of rotation Aj is obtained. Thus, on the circle Cn, for a rotation of angle Aj starting from the seeding line LR, a point Pn is obtained which represents the end of the portion dn on the corresponding circumference of circle Cn.

Figure 3:
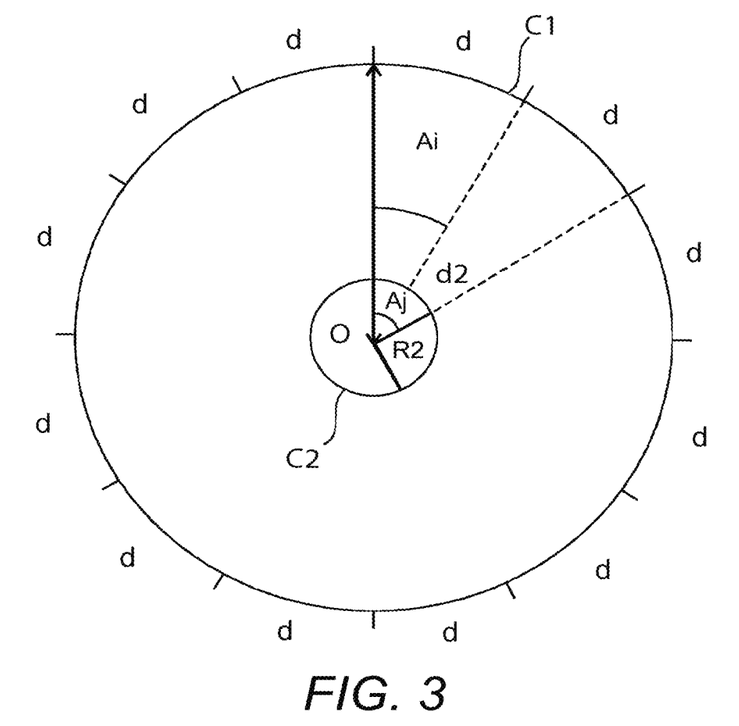
FIG. 3 shows a second detailed schematic representation of a locating means under development, according to an embodiment of the invention, by way of example.

Thus, as shown in FIG. 3, a rotation of the seeding device by an angle Ai represented by a portion d on circle C1 corresponds to a rotation of the comb by an angle Aj to obtain a portion of length d2 identical to d on circle C2.

Therefore, we obtain Aj=d2/RC2, where d2=d=Ai×R, which makes it possible to define the angle Aj associated with distance d2 on circle C2, such that Aj=(Ai×R)/RC2.

Thus, by repeating this method on all of the circles Cn, there is obtained a point Pn+1 on circle Cn+1, a point Pn+2 on circle Cn+2, and so on on all of the circles Cn as shown in FIG. 2.

For each rotation of the seeding device, the associated points P1 and P2 on circles C1 and C2 are defined.

For a same angle of rotation Ai, all of the points Pn, Pn+1, Pn+2, etc. associated with a same zone Zn, are connected together as shown in FIG. 2 to form a line. The end of this line is connected to points P1 and P2, respectively situated on circles C1 and C2, to obtain the representation of a locating zone Zn such as shown in FIG. 2. The locating zone Zn contains a quantity of fluid associated with a movement of the seeding device over a same distance d.

Thus, during the rotation by an angle Ai of the seeding device, the point of contact of the contact zone travels an azimuthal distance d on the circumference of circle C1. Zone Z1 makes it possible to locate the quantity of fluid which has travelled the same distance d from the seeding line LR. Each zone Zn is located on the circumference of circle C1 by an azimuthal distance equal to d.

The seeding device makes a set number of rotations of angle Ai vis-à-vis the base of the Petri dish. These rotations of angle Ai make it possible to spread on the culture medium the entirety of the fluid contained in the seeding line LR.

Figure 4:
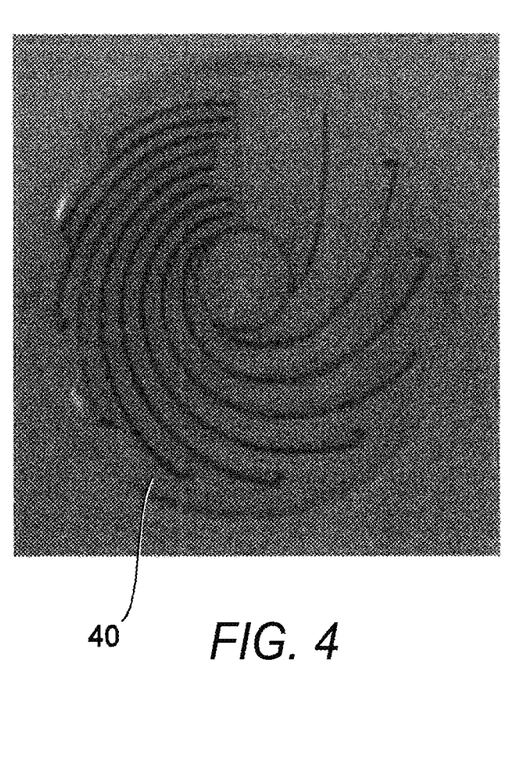
FIG. 4 shows a schematic representation of a locating means integrated onto the lid of a Petri dish.
Figure 5:
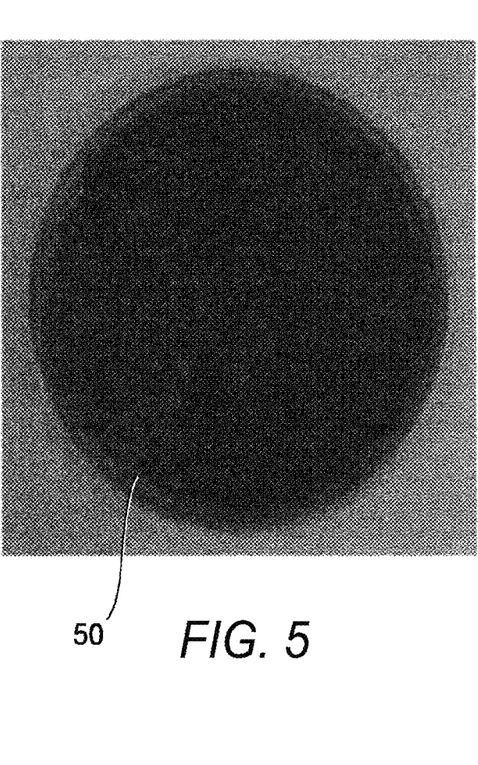
FIG. 5 shows a Petri dish base comprising an agar medium, according to an embodiment of the invention, by way of example.

Conveniently, the locating means 10 may have an independent support to be applied onto the lid of a Petri dish after incubation of the Petri dish. Alternatively, a lid of a Petri dish may integrate a graphic representation of the locating means 10. Thus, FIG. 4 shows a lid 40 of a Petri dish integrating a graphic representation of the various locating zones. FIG. 5 shows a base 50 of a Petri dish containing an agar culture medium. Thus, the lid 40 may be placed on the base 50 in order to locate the microorganisms on the agar culture medium.

Figure 6:
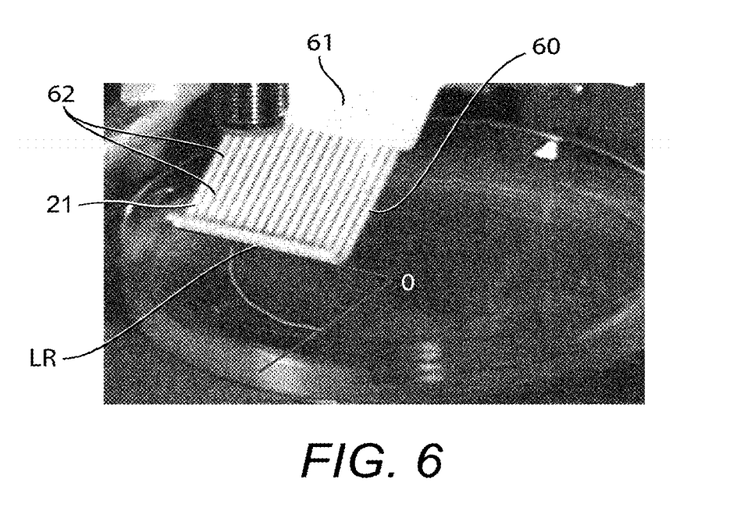
FIG. 6 shows a seeding device, such as a comb, situated above a Petri dish base, according to an embodiment of the invention, by way of example.

As shown in FIG. 6, a seeding device such as a comb 60 is placed above the base 50 of a Petri dish. The base 50 is represented by a circle C1 with a centre O. The base 50 can be mounted on a support capable of moving in a circular movement in order to produce a rotation of the base 50. The base 50 contains a culture medium such as an agar culture medium. A seeding line LR of length R is placed on the culture medium.

The comb 60 comprises one teeth support 61 equipped with a plurality of teeth 62 comprising at least one tooth. Preferably, the comb 60 comprises 17 teeth. Each tooth 62 is separated from an adjacent tooth by a same distance. The total width of the comb 60 corresponds to a value smaller than the length R of the seeding line. The comb 60 is able to rotate relative to the base 50 of the Petri dish.

The locating method according to the invention makes it possible to locate microorganisms present within a fluid on the culture medium, after incubation of the Petri dish. The fluid comprises, for example, a biological sample as mentioned previously. For the purposes of the present example, we shall consider the hypothesis wherein the length R of the seeding line LR is equal to the radius RC1 of the Petri dish.

Figure 7:
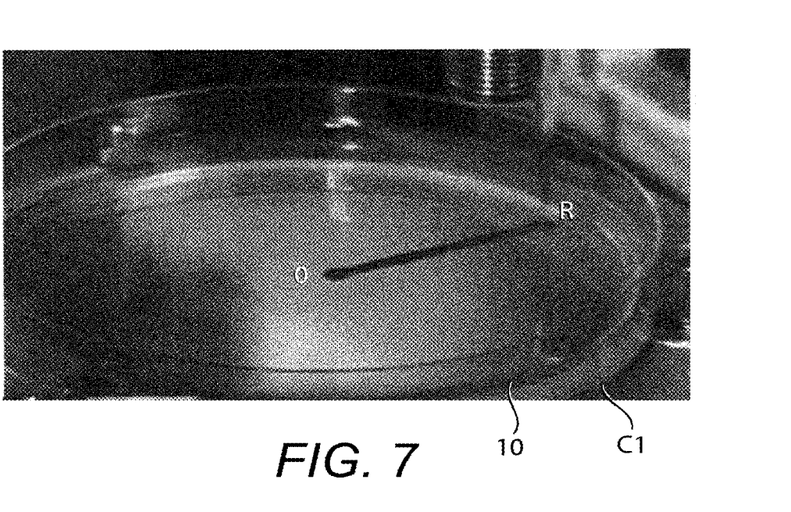
FIG. 7 shows a fluid strip placed on the culture medium on the base of the Petri dish, according to an embodiment of the invention, by way of example.
Figure 8:
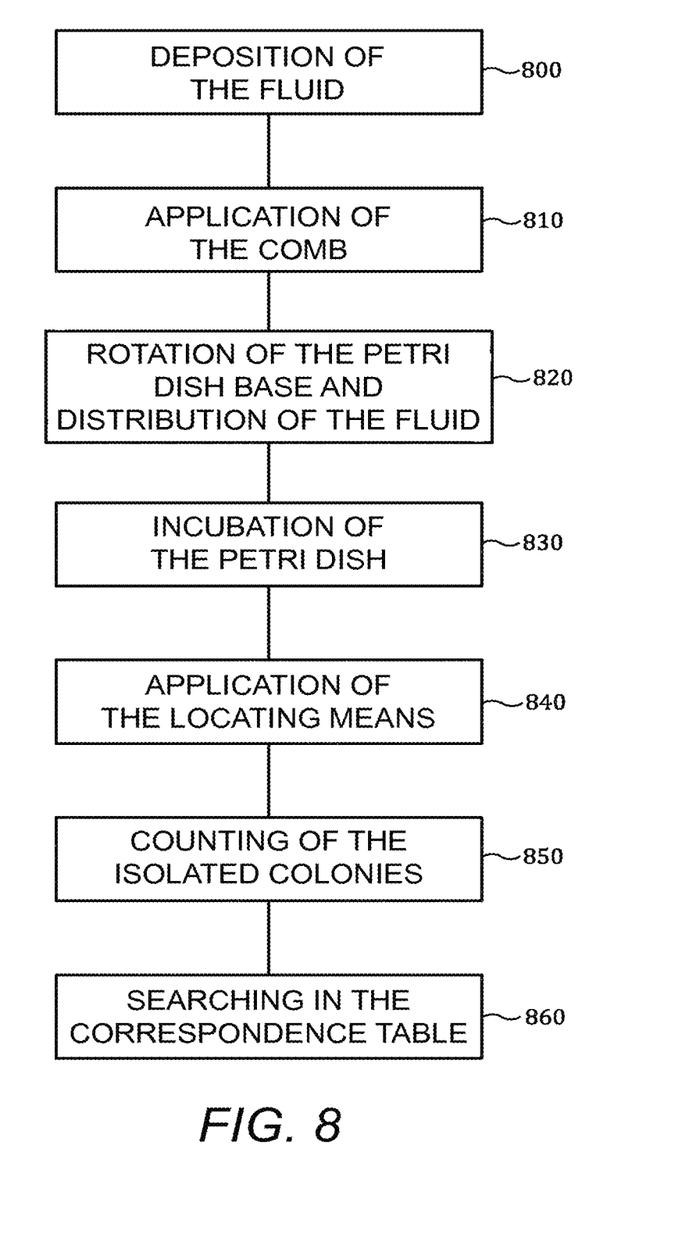
FIG. 8 shows a diagram of the steps of the locating method, according to an embodiment of the invention, by way of example.

The method according to the invention comprises the steps described in FIG. 8. In a step 800, an inoculation device (not shown), controlled for example by a computer program by means of a computer, deposits a quantity of fluid in the form of a seeding line LR onto the culture medium as shown in FIG. 7. The seeding line LR extends over the base 50 of the Petri dish, in the direction of the radius RC1 of the Petri dish.

In a known manner, in a step 810, the comb 60 is applied onto the fluid situated on the seeding line LR. The comb 60 and the base 50 of the Petri dish are designed to work together in the following manner: during a rotation of the base 50, the comb 60 comes into contact with the seeding line LR. Thus, in a step 820, the base of the Petri dish starts to rotate and the comb 60 distributes, on the culture medium, the fluid contained in the seeding line LR. The comb 60 can be preset to make, relative to the base 50 of the Petri dish, repeated rotations centred on the centre O of the base 50 of the Petri dish, and of a same angle Ai.

During the movement of the comb, only the tooth 21 situated on the periphery of the base 50 of the Petri dish moves by an azimuthal distance d on the circumference of the circle C1 such that d=R×Ai. The other teeth 62 of the comb 60 travel an azimuthal distance, the length of which is lower than d. Thus, for a same comb 60, the fictitious angle of rotation Aj of each tooth 62 situated strictly inside the circle C1 must be larger than the actual angle of rotation Ai, so that each tooth 62 travels an azimuthal distance identical to d on the corresponding concentric circle Cn. Indeed, as we consider a tooth 62 nearer to the centre O of the circle C1, the azimuthal distance travelled by the tooth 62 decreases, for a given angle of rotation Ai.

The movement of the comb 60 associated with the movement of the base of the Petri dish is repeated until the totality of the contents of the fluid of the seeding line LR is distributed on the agar culture medium.

Then, in a step 830, the base 50 of the Petri dish covered by a lid suitable for a Petri dish is incubated in an incubator for a predetermined period. The aim of the incubation is to enable the growth of microorganisms potentially contained in the fluid distributed on the culture medium. The incubation period can extend over several hours or over several days, preferably over twenty-four hours. This incubation period can be continuous, i.e. without intermediate analysis of the contents of the Petri dish, between the inoculation of the biological sample and the end of the incubation period. The incubation period can also be discontinuous, i.e. with a regular analysis of the contents of the Petri dish at predetermined times during the incubation period.

The steps 810, 820 and 830 previously described can be carried out by means of an automated device controlled by a computer program by means of a computer.

At a predetermined time, either during the incubation period or at the end of the incubation period, in a step 840, the locating means 10 according to the present invention is applied onto the Petri dish. Step 840 can be performed either manually, or automatically by means of a mechanical device controlled by a computer program, or electronically using the image of a locating means to be applied onto an image of the Petri dish by means of an electronic device such as a computer.

After incubation, the culture medium, in the base 50 of the Petri dish, contains colonies of microorganisms situated at different locations on the surface of the culture medium. Certain colonies can appear isolated and therefore be easily counted visually by the user. Other colonies can be amassed and be impossible to count. In a situation in which the value of the microorganism concentration per millilitre (ml) is greater than a concentration of around $10^3$ microorganisms per ml, preferably greater than a concentration equal to $10^3$ microorganisms per ml, the distribution of the colonies is represented by continuous zones of colonies on the culture medium. In this case, the use of the locating means 10 according to the present invention is optimal.

In a step 850, the user can visually count the isolated colonies within the locating zones of the locating means 10. Step 850 can also be performed by means of an automated device controlled by a computer program with reference to an image processing method, using the image of a locating means applied onto an image of the Petri dish, by means of an electronic device such as a computer.

Then, in a step 860, the user searches for the value of the concentration associated with the number of isolated colonies counted in a zone under consideration using, for example, the correspondence table below:

| Concentration in CFU/ml (CFU: Colony Forming Unit) | Number of isolated colonies located in a locating zone |
|---|---|
| $10^2$ | Less than 10 colonies |
| $10^3$ | Less than 30 colonies |
| $10^4$ | Greater than 30 colonies and locating zone Z1 is not full |
| $10^5$ | Locating zone Z1 filled (no isolated colony) Locating zone Z2 and Z3 containing isolated colonies |
| $10^6$ | Locating zone Z1 and Z2 filled (no isolated colony) Locating zones Z3 and Z4 containing isolated colonies |
| $10^7$ | Locating zone Z1, Z2 and Z3 filled (no isolated colony) Locating zone Z4 containing isolated colonies |
| $10^8$ | Locating zone Z1, Z2, Z3 and Z4 filled (no isolated colony) Locating zone Z5 containing isolated colonies |

The concentration values presented in the table above are obtained using the mathematical formula $C(RC_n, A) = C_o \exp(-RC_n \times A/K)$ which defines the distribution of microorganism concentration on the culture medium. In this mathematical formula:

A is the value of the actual angle of rotation of the seeding device (60);

$C_o$ is the initial microorganism concentration of the inoculated fluid;

$RC_n$ is the radius of the concentric circle under consideration;

K is a depletion constant specific to a fluid relative to the agar culture medium on which the fluid is distributed.

Step 860 can be performed by means of a computer containing a suitable computer program.

Thus, steps 800, 810, 820, 830, 840, 850 and 860 can be performed in an automated manner.

Figure 9:
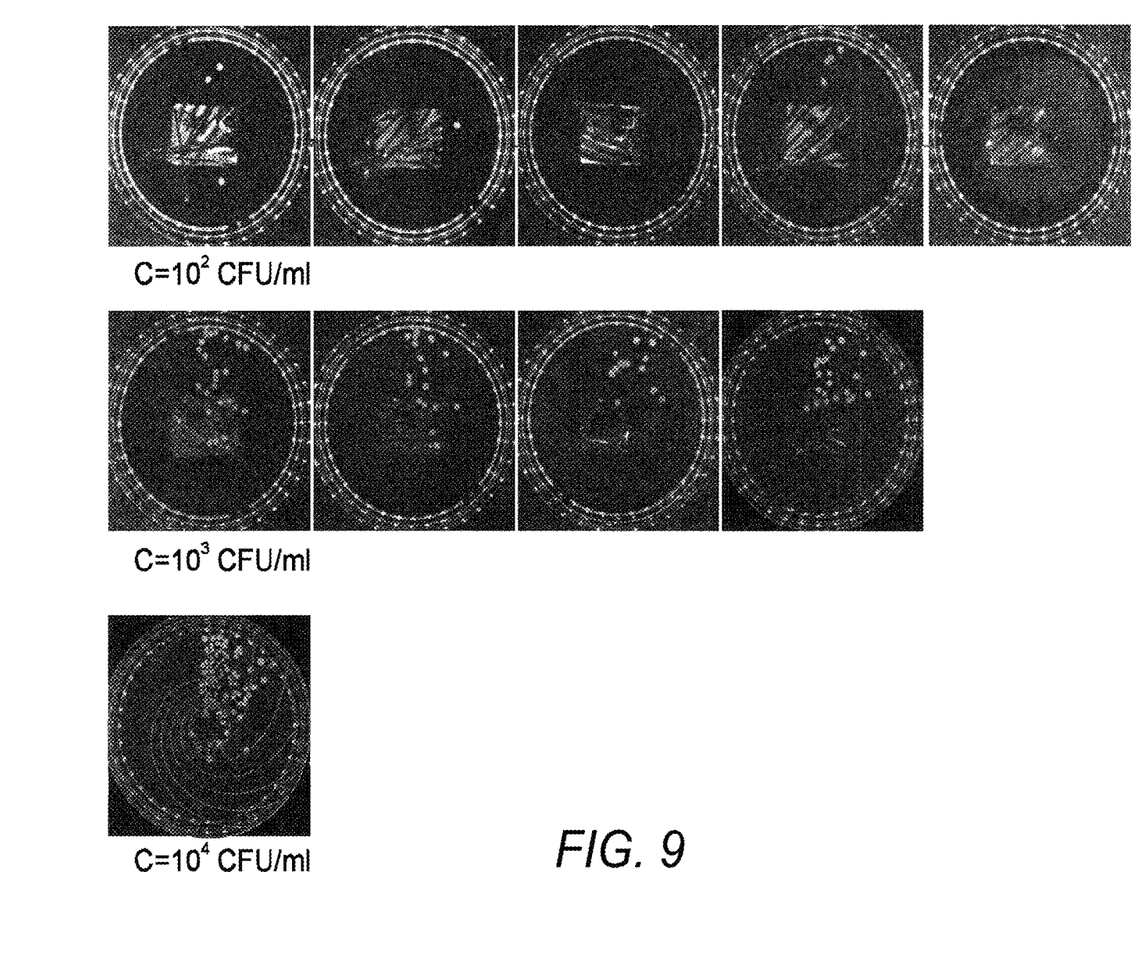
FIGS. 9, 10 and 11 show examples of application of the locating means onto the contents of various Petri dishes containing various types of fluids with various concentrations of microorganisms.
Figure 10:
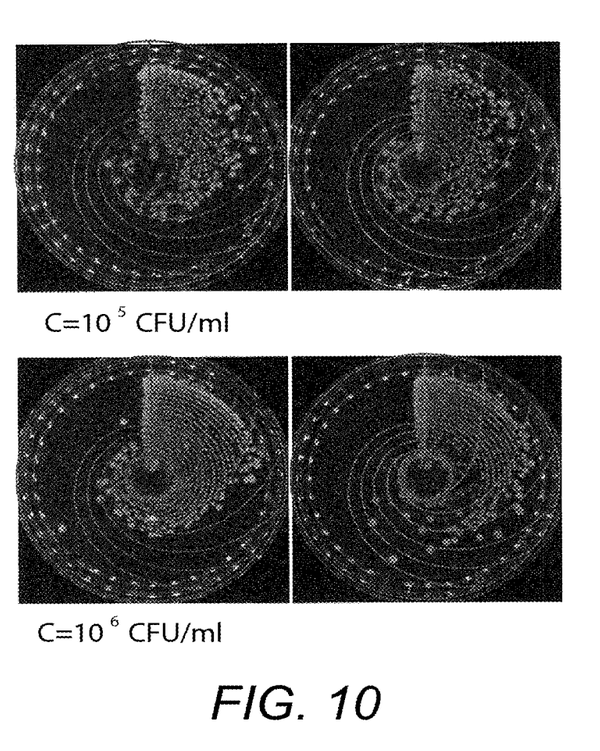
Figure 11:
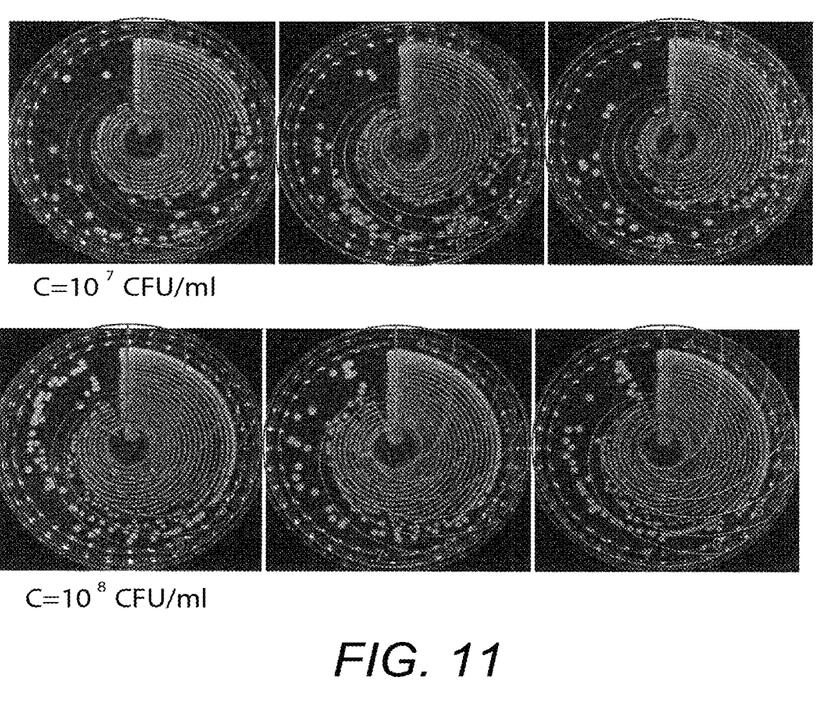

FIGS. 9, 10 and 11 show examples of application of the locating method for urinary samples.

FIG. 9 shows progressive concentrations from $10^2$ to $10^4$ CFU/ml on TSA agar (Tryptic Soy Agar).

FIG. 10 shows progressive concentrations from $10^5$ to $10^6$ CFU/ml on TSA agar.

FIG. 11 shows progressive concentrations from $10^7$ to $10^8$ CFU/ml on TSA agar.

Figure 12:
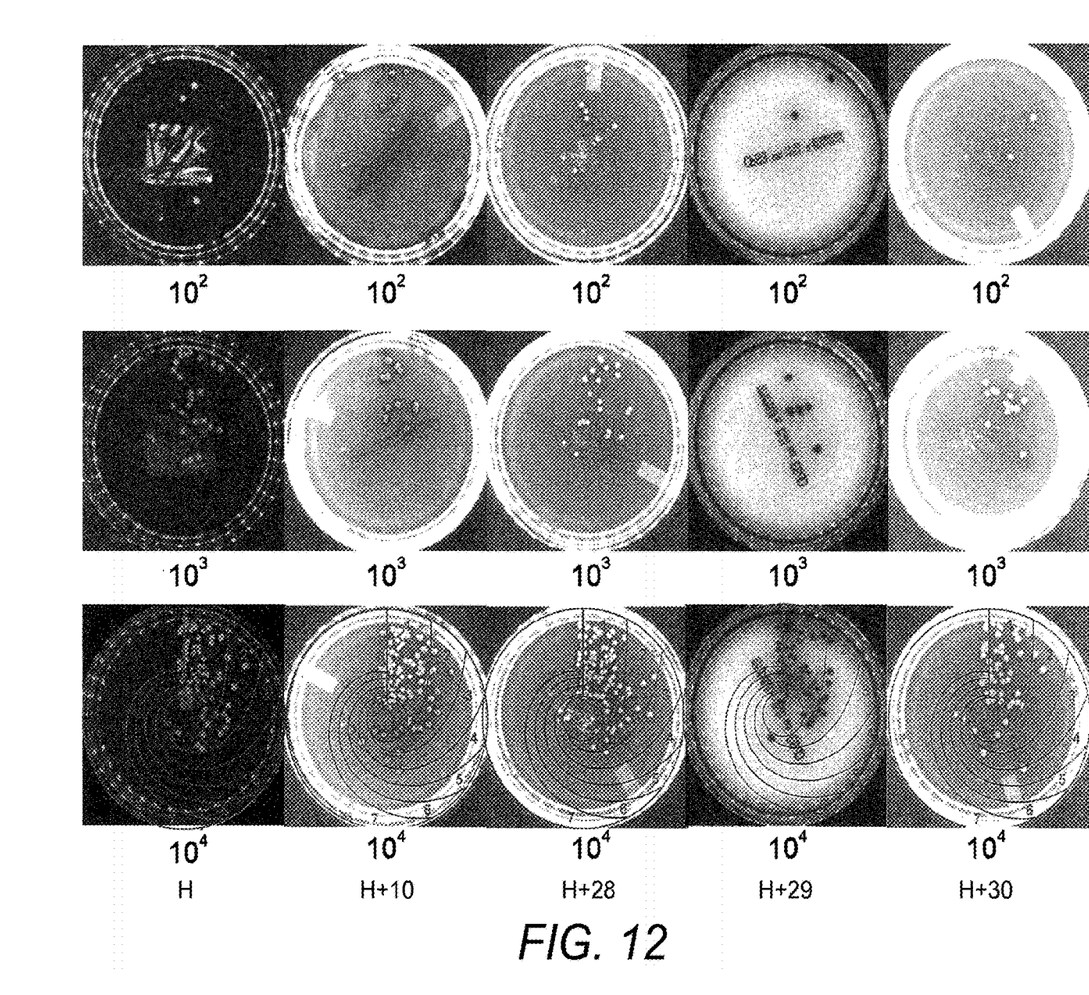
FIGS. 12, 13 and 14 show examples of application of the locating means onto the contents of various Petri dishes during the analysis of various types of fluid over time.
Figure 13:
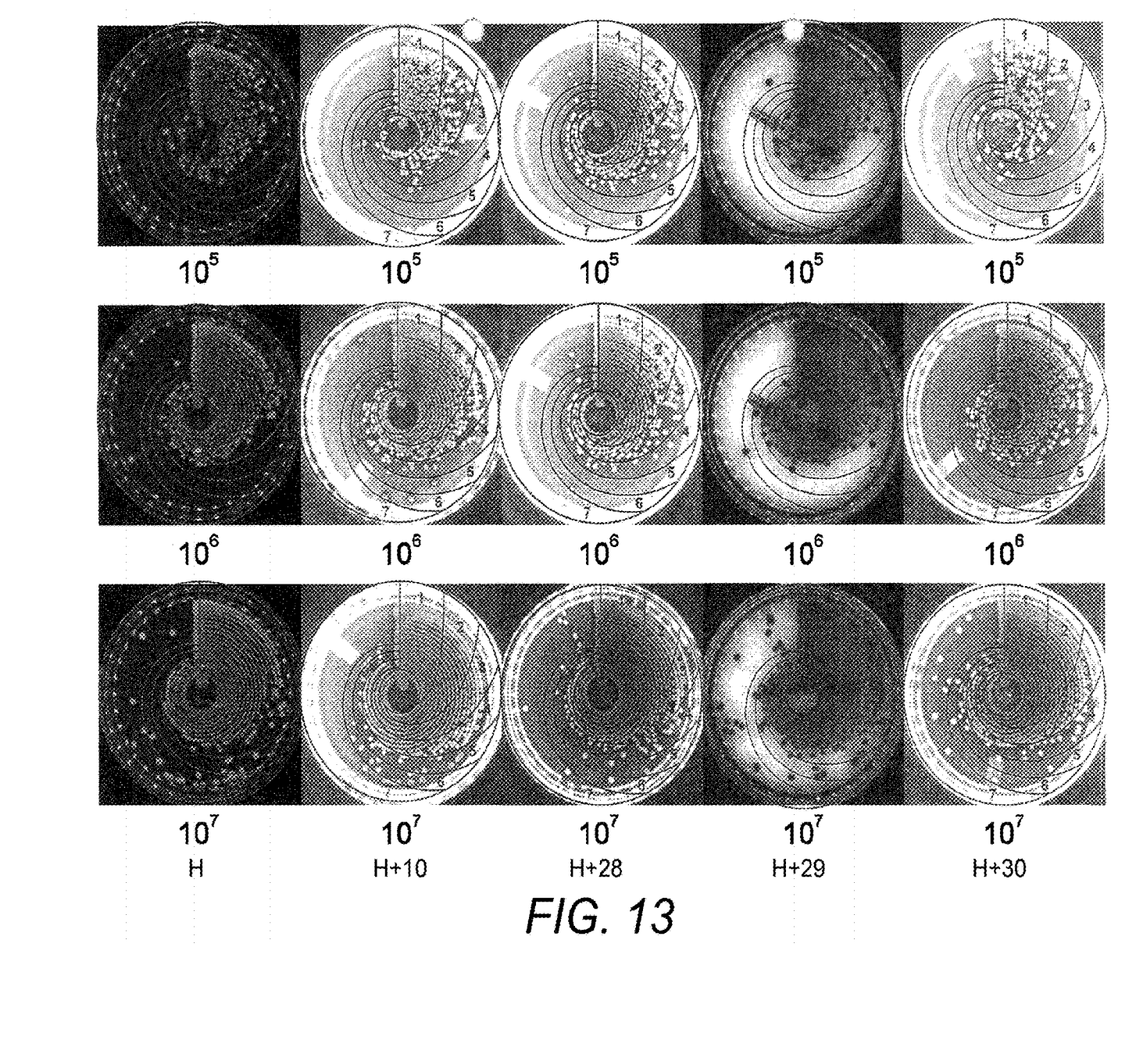
Figure 14:
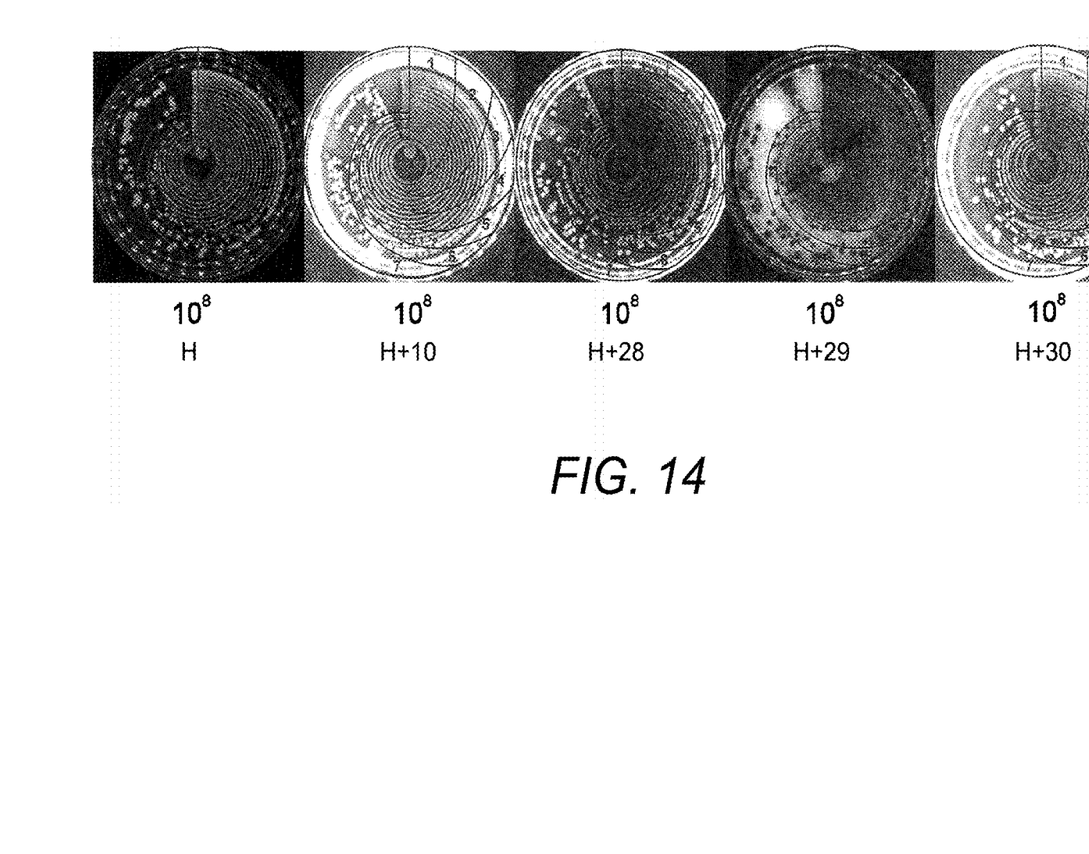

Similarly, FIGS. 12, 13 and 14 show an example of analysis of a same fluid at different concentrations ($10^2$ to $10^8$ CFU/ml) inoculated on ChromID™ CPS® medium at different successive moments in time. Thus, taking a number of hours as a basis, it is possible to observe the evolution of the microorganism concentration at a given time H, then successively at a time H+10 hours, H+26 hours, and so on, for example. This involves extemporaneous preparation of bacterial solution. Thus, the reproducibility of the locating method can be estimated.

In total, 122 dishes have been tested with the method according to the present invention on ChromID™ CPS® medium, i.e. a medium dedicated to urine counting, for which this method is extremely useful. The threshold concentration value was $10^4$ CFU/ml.

As shown in the table below, a sensitivity and a specificity of 100% is obtained relative to the theoretical bacterial concentration.

|  |  | Estimation with the locating means according to the present invention. | | | |
|---|---|---|---|---|---|
|  |  | Negative | Uncertainty | Positive | Total |
| Theory | Negative (<$10^4$ CFU/ml) | 40 | 0 | 0 | 40 |
|  | Uncertainty (=$10^4$ CFU/ml) | 0 | 18 | 0 | 18 |
|  | Positive (>$10^4$ CFU/ml) | 0 | 0 | 59 | 59 |
|  | Total | 40 | 18 | 59 | 117 |

The present invention is specifically suitable for the seeding devices described previously or for seeding devices which have a similar mode of operation concerning the distribution of the fluid on a culture medium suitable for the mode of distribution.

Such seeding devices comprise, for example, devices which are able to rotate relative to the centre of the Petri dish and which make it possible to radially deposit the fluid by means of radial extension.

The invention claimed is:

1. A locating method for determining the microorganism concentration of a fluid in a Petri dish with a first radius, the Petri dish containing a culture medium, the method comprising:

depositing the fluid onto the culture medium to form a seeding line corresponding to a portion of the first radius of the Petri dish;

distributing the fluid contained in the seeding line onto the culture medium by means of a seeding device rotating relative to the Petri dish, the seeding device comprising at least one point of contact with the culture medium;

incubating the Petri dish to permit the growth of the microorganisms on the culture medium; and identifying adjacent locating zones to locate the presence of microorganisms on the surface of the culture medium, the locating zones covering at least part of the surface of the Petri dish and in which a first locating zone is delimited by the seeding line and a zone boundary line delimiting an identical azimuthal distance travelled on the culture medium by each point of contact of the seeding device starting from the seeding line, wherein the identical azimuthal distance corresponds to movement of the at least one point of contact from the seeding line during notation of the device.

2. The locating method of claim 1, wherein the fluid comprises a microorganism concentration greater than $10^3$ microorganisms per milliliter.

3. The locating method of claim 1, the method further comprising:

identifying a second locating zone comprising isolated colonies of microorganisms.

4. The locating method of claim 3, the method further comprising:

finding, in a correspondence table, a predetermined value for microorganism concentration associated with the identified locating zone in order to determine the microorganism concentration in the fluid.

5. The locating method of claim 1, the method further comprising identifying isolated colonies of microorganisms in the first locating zone.

* * * * *